(12) United States Patent
Lim et al.

(10) Patent No.: US 8,946,785 B2
(45) Date of Patent: Feb. 3, 2015

(54) IONIC FIELD EFFECT TRANSISTOR HAVING HETEROGENEOUS TRIANGULAR NANOCHANNEL AND METHOD OF MANUFACTURING THE SAME

(71) Applicant: Postech Academy-Industry Foundation, Pohang-si (KR)

(72) Inventors: Geunbae Lim, Pohang-si (KR); Sung Jae Kim, Seoul (KR); Bumjoo Kim, Pohang-si (KR); Joonseong Heo, Pohang-si (KR); Hyukjin J. Kwon, Yongin-si (KR)

(73) Assignee: Postech Academy-Industry Foundation, Pohang-Si (KR)

( * ) Notice: Subject to any disclaimer, the term of this patent is extended or adjusted under 35 U.S.C. 154(b) by 0 days.

(21) Appl. No.: 14/181,820

(22) Filed: Feb. 17, 2014

(65) Prior Publication Data

US 2014/0238521 A1 Aug. 28, 2014

(30) Foreign Application Priority Data

Feb. 22, 2013 (KR) .......................... 10-2013-0019382

(51) Int. Cl.
*G01N 27/414* (2006.01)
*B82Y 15/00* (2011.01)

(52) U.S. Cl.
CPC ............ *G01N 27/4146* (2013.01); *B82Y 15/00* (2013.01)
USPC .............................................. 257/253; 438/49

(58) Field of Classification Search
CPC .................................................. G01N 27/4146
See application file for complete search history.

(56) References Cited

FOREIGN PATENT DOCUMENTS

| KR | 10-2008-0030297 | 4/2008 |
| KR | 10-2011-0009643 | 1/2011 |
| KR | 10-2012-0000520 | 1/2012 |

*Primary Examiner* — Erik Kielin
(74) *Attorney, Agent, or Firm* — Lexyoume IP Meister, PLLC

(57) ABSTRACT

An ionic field effect transistor includes: a substrate; a polymer layer that is formed on the substrate and in which a first flow path and a second flow path that is separately disposed from the first flow path are formed; and a gate electrode that is formed between the substrate and the polymer layer and that contacts the first flow path and the second flow path, wherein a heterogeneous triangular nanochannel that connects the first flow path and the second flow path is formed between the gate electrode and the polymer layer.

9 Claims, 6 Drawing Sheets

IONIC FIELD EFFECT TRANSISTOR HAVING HETEROGENEOUS TRIANGULAR NANOCHANNEL AND METHOD OF MANUFACTURING THE SAME

CROSS-REFERENCE TO RELATED APPLICATION

This application claims priority to and the benefit of Korean Patent Application No. 10-2013-0019382 filed in the Korean Intellectual Property Office on Feb. 22, 2013, the entire contents of which are incorporated herein by reference.

BACKGROUND OF THE INVENTION (a) Field of the Invention

The present invention relates to an ionic field effect transistor having a heterogeneous triangular nanochannel, and a method of manufacturing the same.

(b) Description of the Related Art

Unlike a microchannel, because a nanochannel has a very high value in a ratio of a wall surface area to a cross-sectional area of a channel, a surface charge or a surface potential of a wall surface has a great influence on flow of ions. Technology that changes a gate potential value and variously controls flow of ions by manufacturing a nanochannel and inserting a gate electrode into the bottom using such a phenomenon forms an ionic field effect transistor (Ifet).

In general, an ionic field effect transistor chip is produced by elaborately manufacturing a nanochannel using a material such as PDMS or silicon and aligning and bonding the nanochannel on a substrate such as glass in which a gate electrode is patterned.

However, a drawback of such a manufacturing method is that expensive and elaborate equipment is necessary when manufacturing a nanochannel and that a gate electrode should be previously formed at a substrate to bond to the nanochannel. Further, when physically bonding the nanochannel and the gate electrode, precise aligning and positioning should be followed.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide an ionic field effect transistor and a method of manufacturing the same having an advantage of being capable of easily producing it.

An exemplary embodiment of the present invention provides an ionic field effect transistor including: a substrate; a polymer layer that is formed on the substrate and in which a first flow path and a second flow path that is separately disposed from the first flow path are formed; and a gate electrode that is formed between the substrate and the polymer layer and that contacts the first flow path and the second flow path, wherein a heterogeneous triangular nanochannel that connects the first flow path and the second flow path is formed between the gate electrode and the polymer layer.

The ionic field effect transistor may further include an insulating layer that is formed to cover the substrate and the gate electrode on the substrate, wherein the heterogeneous triangular nanochannel may be formed at an interface of the insulating layer and the polymer layer.

In the polymer layer, a first fluid injection opening that is connected to an end portion of one side of the first flow path and a first electrode inlet that is connected to an end portion of the other side of the first flow path may be formed.

In the polymer layer, a second fluid injection opening that is connected to an end portion of one side of the second flow path and a second electrode inlet that is connected to an end portion of the other side of the second flow path may be formed.

The flow path may be formed in a groove form at a surface facing the substrate in the polymer layer.

The heterogeneous triangular nanochannel may be formed by an insulating layer that covers an upper surface of the substrate, an insulating layer that is protruded to cover a side surface of the gate electrode, and a lower surface of the polymer layer that is connected from the protruded insulating layer to an insulating layer on the substrate.

The gate electrode may be formed with a metal having conductivity.

Another embodiment of the present invention provides a method of manufacturing an ionic field effect transistor, the method including: forming a polymer layer having a first flow path and a second flow path that is separately disposed from the first flow path; forming a gate electrode that is connected in one direction on a substrate and that is made of a metal; and forming a heterogeneous triangular nanochannel that is enclosed by the polymer layer and the substrate and the gate electrode by bonding the polymer layer and the substrate.

The method may further include forming an insulating layer to cover the gate electrode on the substrate.

According to an ionic field effect transistor of the present exemplary embodiment, by conducting ions using a heterogeneous triangular nanochannel, an ionic field effect transistor having a heterogeneous triangular nanochannel can be easily produced.

DETAILED DESCRIPTION OF THE EMBODIMENTS

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Figure 1:
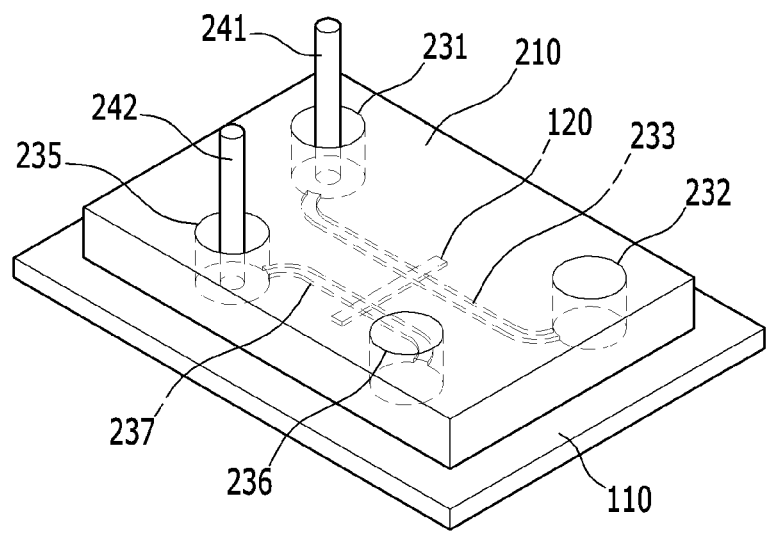
FIG. 1 is a perspective view illustrating an ionic field effect transistor according to an exemplary embodiment of the present invention.
Figure 2:
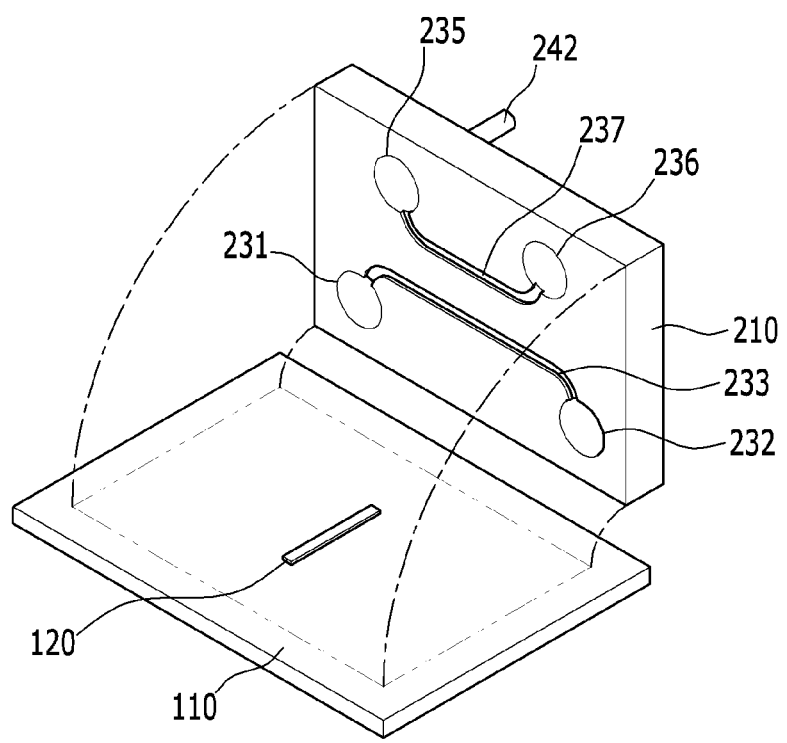
FIG. 2 is an exploded perspective view illustrating an ionic field effect transistor according to an exemplary embodiment of the present invention.
Figure 3:
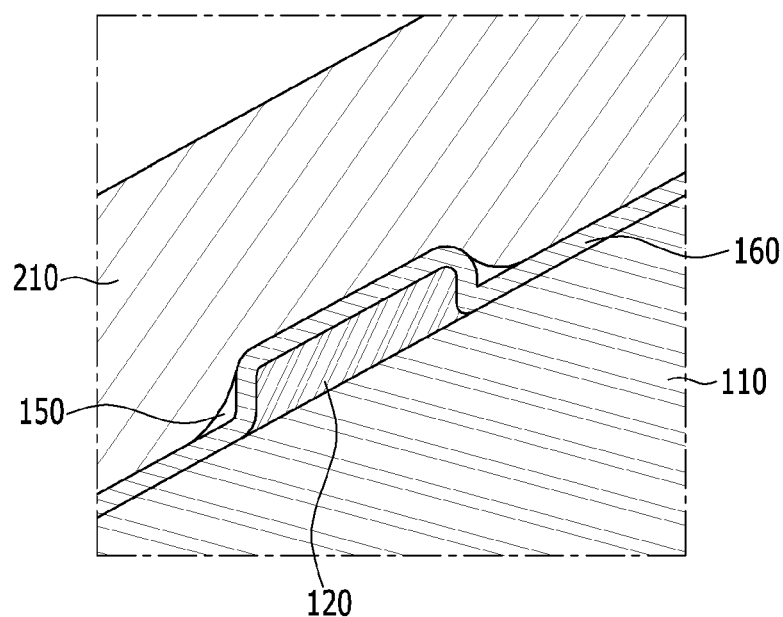
FIG. 3 is a cross-sectional view illustrating a heterogeneous triangular nanochannel according to an exemplary embodiment of the present invention.

FIG. 1 is a perspective view illustrating an ionic field effect transistor according to an exemplary embodiment of the present invention, FIG. 2 is an exploded perspective view illustrating an ionic field effect transistor according to an exemplary embodiment of the present invention, and FIG. 3 is a cross-sectional view illustrating a heterogeneous triangular nanochannel according to an exemplary embodiment of the present invention.

Referring to FIGS. 1 to 3, an ionic field effect transistor 100 according to the present exemplary embodiment includes a substrate 110, a polymer layer 210 that is formed on the substrate 110, and a gate electrode 120 that is formed between the polymer layer 210 and the substrate 110. A heterogeneous triangular nanochannel 150 is formed at an interface of a side surface of the polymer layer 210 and the gate electrode 120.

The substrate 110 may be formed in a flat plate form like a glass substrate or a silicon wafer, and may be a flat film. The polymer layer 210 is made of a polymer material having appropriate mechanical elasticity like polydimethylsiloxane (PDMS), and has a first fluid injection opening 232, a first electrode inlet 231, a second electrode inlet 235, and a second fluid injection opening 236.

Further, a first flow path 233 that connects the first fluid injection opening 232 and the first electrode inlet 231 and a second flow path 237 that connects the second electrode inlet 235 and the second fluid injection opening 236 are formed in the polymer layer 210. The first flow path 233 and the second flow path 237 are formed in a groove form at a surface facing the substrate 110 in the polymer layer 210. The first flow path 233 and the second flow path 237 are separately disposed by a predetermined gap, and have a portion that is separately disposed in parallel.

The first fluid injection opening 232 is connected to an end portion of one side of the first flow path 233, and the first electrode inlet 231 is connected to an end portion of one side of the first flow path 233. Further, the second fluid injection opening 236 is connected to an end portion of one side of the second flow path 237, and the second electrode inlet 235 is connected to an end portion of the other side of the second flow path 237.

The gate electrode 120 may be formed in a structure that is straight line, a vertically bent structure, or a streamlined curve, and contacts the first flow path 233 and the second flow path 237 to connect the first flow path 233 and the second flow path 237. The gate electrode 120 may be made of various metal materials having conductivity such as copper and aluminum. The gate electrode 120 may be made of a conductive material that may be deposited in a thickness of 2 μm or less. The gate electrode 120 may be formed with a method such as deposition or coating.

An insulating layer 160 is formed on the gate electrode 120, and the insulating layer 160 is formed to cover the substrate 110 and the gate electrode 120. The insulating layer 160 may be made of a polymer having an insulating property and may be formed to have a thickness of several tens of nanometers to several hundreds of nanometers.

A positive terminal 241 is installed at the first electrode inlet 231, and a negative terminal 242 is installed at the second electrode inlet 235. The positive terminal 241 and the negative terminal 242 are formed as a metal bar having conductivity, and a voltage may be applied to the positive terminal 241 and the negative terminal 242 or a voltage and a current may be measured through the positive terminal 241 and the negative terminal 242.

When the polymer layer 210 is bonded to the substrate 110 having the gate electrode 120, a heterogeneous triangular nanochannel 150 is formed, as shown in FIG. 3. The heterogeneous triangular nanochannel 150 is enclosed by the substrate 110 and the insulating layer 160 to be formed to have a vertical section of an approximate triangle, and the heterogeneous triangular nanochannel 150 connects the first flow path 233 and the second flow path 237. The heterogeneous triangular nanochannel 150 is formed by the insulating layer 160 that covers an upper surface of the substrate 110, the insulating layer 160 that is protruded to cover a side surface of the gate electrode 120, and a lower surface of the polymer layer 210 that is connected from the protruded insulating layer 160 to the insulating layer 160 on the substrate 110.

Such a heterogeneous triangular nanochannel 150 has a small cross-sectional area that is sufficient to selectively transmit ions, and is formed to connect in a direction toward the second flow path 237 from the first flow path 233. In this way, according to the present exemplary embodiment, a nanochannel that can easily selectively transmit ions without forming a separate channel or without using Nafion can be formed.

Hereinafter, a method of manufacturing an ionic field effect transistor 100 will be described.

A method of manufacturing the ionic field effect transistor 100 according to the present exemplary embodiment includes a step of forming the polymer layer 210 having the first flow path 233 and the second flow path 237, a step of forming the gate electrode 120 that is long connected on the substrate 110, a step of forming the insulating layer 160 to cover the gate electrode 120 on the substrate, and a step of forming the heterogeneous triangular nanochannel 150 that is enclosed by the polymer layer 210 and the insulating layer 160 by bonding the polymer layer 210 and the substrate 110.

The step of forming the polymer layer 210 includes a step of manufacturing a mold having a flow path pattern on a silicon wafer, a step of injecting a polymer into the mold, a step of hardening the polymer, and a step of forming an injection opening in the polymer layer 210.

At the step of manufacturing a mold, a pattern for forming a channel is formed using photolithography on a silicon wafer. In this case, a height of the pattern may be about 15 μm.

At the step of injecting the polymer into the mold, PDMS and a cross-linker are mixed at 10:1 wt % and are injected into the frame. At the step of hardening the polymer, the polymer layer 210 is hardened by heating for about 3 hours in an oven at 65° C. At the step of forming an injection opening, after the mold and the polymer layer 210 are separated, four holes are formed at predetermined positions using a punch.

At the step of forming the gate electrode 120, the gate electrode 120 is formed on the substrate 110, and by coating a conductive material having a thickness of 2 μm or less with various methods, the gate electrode 120 is formed.

At the step of forming the insulating layer 160, in order to cover the gate electrode 120 on the substrate 110, the insulating layer 160 is formed with a method such as deposition and coating, and by coating an insulation material having a thickness of several tens of nanometers with various methods, the insulating layer 160 is formed.

At the step of forming the heterogeneous triangular nanochannel 150, by performing plasma surface processing at a surface of the polymer layer 210 and a surface of the insulating layer 160, a hydroxyl group (—OH) is formed, and the polymer layer 210 and the substrate 110 are bonded using the hydroxyl group (—OH). When the polymer layer 210 and the substrate 110 are bonded, the heterogeneous triangular nanochannel 150 is formed due to the gate electrode 120. The heterogeneous triangular nanochannel 150 is formed by the insulating layer 160 that covers an upper surface of the substrate 110, the insulating layer 160 that is protruded to cover a side surface of the gate electrode 120, and a lower surface of the polymer layer 210 that is connected from the protruded insulating layer 160 to the insulating layer 160 on the substrate 110.

When the heterogeneous triangular nanochannel 150 is formed, the terminals 241 and 242 are installed in the first electrode inlet 231 and the second electrode inlet 235, respectively, and a fluid for ion transmission is injected into each of the first fluid injection opening 232 and the second fluid injection opening 236.

According to the present exemplary embodiment, the ionic field effect transistor 100 having the heterogeneous triangular nanochannel 150 can be produced using a simple process that bonds the polymer layer 210 in which the flow paths 233 and 237 are formed and the substrate 110 in which the gate electrode 120 is formed.

Figure 4:
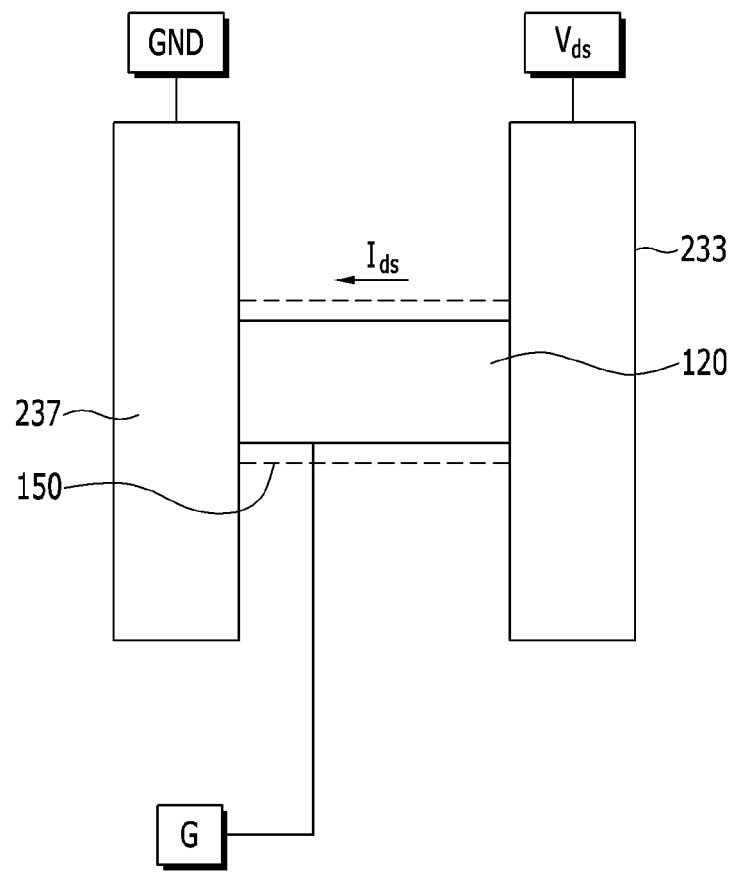
FIG. 4 is a schematic diagram illustrating an ionic field effect transistor according to an exemplary embodiment of the present invention.
Figure 5:
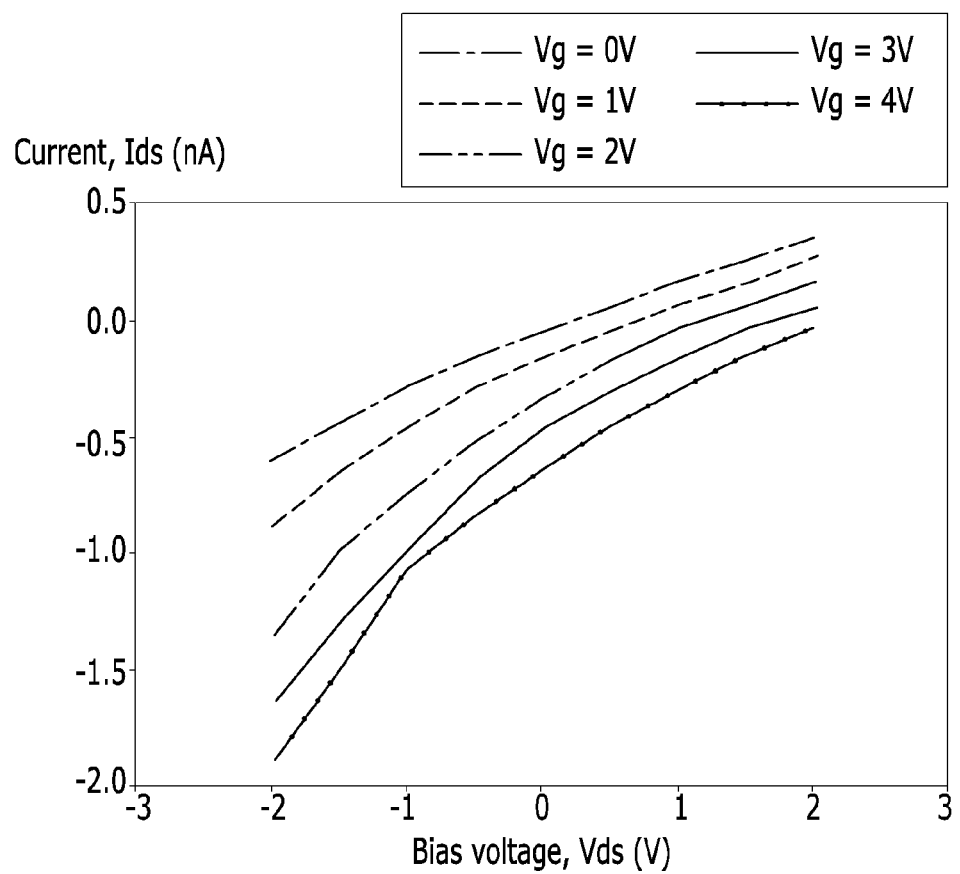
FIG. 5 is a graph showing intensity of a current flowing through a heterogeneous triangular nanochannel according to a voltage that is applied to a gate electrode.

FIG. 4 is a schematic diagram illustrating an ionic field effect transistor according to an exemplary embodiment of the present invention, and FIG. 5 is a graph measuring intensity of a current flowing through a heterogeneous triangular nanochannel according to a voltage that is applied to a gate electrode.

In FIG. 5, a bias voltage Vds represents the difference between voltages that are applied to the positive terminal 241 and the negative terminal 242, a current Ids indicates a current flowing through the heterogeneous triangular nanochannel 150, and a gate voltage Vg is a voltage that is applied to the gate electrode 120. Here, potassium chloride (KCl) is injected into the first fluid injection opening 232 and the second fluid injection opening 236.

When a potential difference occurs in two parallel flow paths 233 and 237 while applying a voltage to the gate electrode 120, flow of ions may be adjusted through the heterogeneous triangular nanochannel 150, and flow of ions is represented with flow of a current.

As shown in FIG. 5, it can be determined that intensity of a current flowing through the heterogeneous triangular nanochannel 150 is sensitively changed according to a voltage that is applied to the gate electrode 120 and a bias voltage. Accordingly, it can be clearly seen that the ionic field effect transistor 100 according to the present exemplary embodiment can be operated according to a voltage that is applied to the gate electrode 120.

Figure 6:
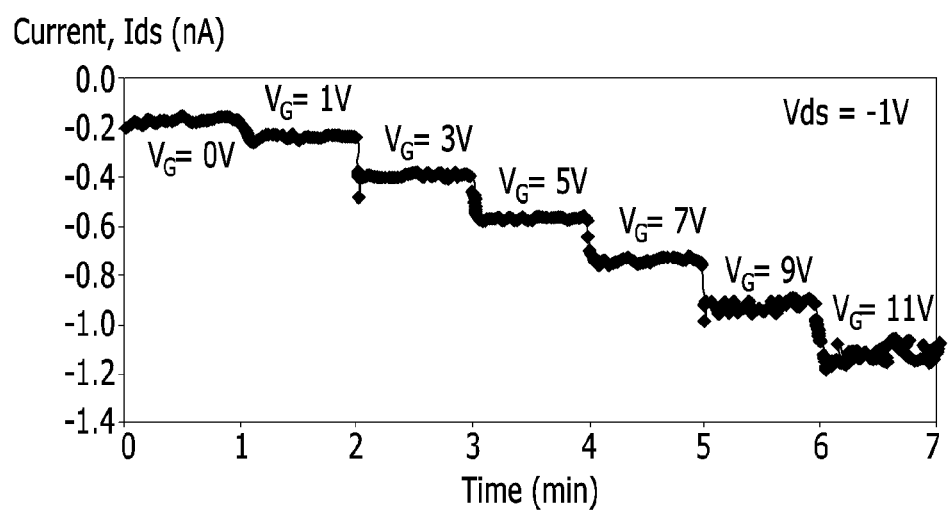
FIG. 6 is a graph illustrating intensity of a current according to a gate voltage when a bias voltage is 1 V.

FIG. 6 is a graph illustrating intensity of a current according to a gate voltage when a bias voltage is 1 V.

As shown in FIG. 6, when a bias voltage is constant, as a voltage that is applied to the gate electrode 120 changes, it can be clearly seen that intensity of a current sensitively reacts, and the ionic field effect transistor 100 according to the present exemplary embodiment is normally operated according to a gate voltage.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of Symbols>

| | |
|---|---|
| 100: ionic field effect transistor | 110: substrate |
| 120: gate electrode | 150: heterogeneous triangular nanochannel |
| 160: insulating layer | 210: polymer layer |
| 231: first electrode inlet | 232: first fluid injection opening |
| 233: first flow path | 235: second electrode inlet |
| 236: second fluid injection opening | 237: second flow path |
| 241: positive terminal | 242: negative terminal |

What is claimed is:

1. An ionic field effect transistor, comprising:
   a substrate;
   a polymer layer that is formed on the substrate and in which a first flow path and a second flow path that is separately disposed from the first flow path are formed; and
   a gate electrode that is formed between the substrate and the polymer layer and that contacts the first flow path and the second flow path,
   wherein a heterogeneous triangular nanochannel that connects the first flow path and the second flow path is formed between the gate electrode and the polymer layer.

2. The ionic field effect transistor of claim 1, further comprising an insulating layer that is formed to cover the substrate and the gate electrode on the substrate,
   wherein the heterogeneous triangular nanochannel is formed at an interface of the insulating layer and the polymer layer.

3. The ionic field effect transistor of claim 2, wherein in the polymer layer, a first fluid injection opening that is connected to an end portion of one side of the first flow path and a first electrode inlet that is connected to an end portion of the other side of the first flow path are formed.

4. The ionic field effect transistor of claim 3, wherein in the polymer layer, a second fluid injection opening that is connected to an end portion of one side of the second flow path and a second electrode inlet that is connected to an end portion of the other side of the second flow path are formed.

5. The ionic field effect transistor of claim 4, wherein the first flow path and the second flow path are formed in a groove form at a surface facing the substrate in the polymer layer.

6. The ionic field effect transistor of claim 2, wherein the heterogeneous triangular nanochannel is formed by an insulating layer that covers an upper surface of the substrate, an insulating layer that is protruded to cover a side surface of the gate electrode, and a lower surface of the polymer layer that is connected from the protruded insulating layer to an insulating layer on the substrate.

7. The ionic field effect transistor of claim 2, wherein the gate electrode is formed with a metal having conductivity.

8. A method of manufacturing an ionic field effect transistor, the method comprising:
   forming a polymer layer having a first flow path and a second flow path that is separately disposed from the first flow path;
   forming a gate electrode that is connected in one direction on a substrate and that is made of a metal; and
   forming a heterogeneous triangular nanochannel that is enclosed by the polymer layer and the substrate and the gate electrode by bonding the polymer layer and the substrate.

9. The method of claim 8, further comprising forming an insulating layer to cover the gate electrode on the substrate.

* * * * *